United States Patent [19]

George et al.

[11] Patent Number: 4,648,944
[45] Date of Patent: Mar. 10, 1987

[54] APPARATUS AND METHOD FOR CONTROLLING PLATING INDUCED STRESS IN ELECTROFORMING AND ELECTROPLATING PROCESSES

[75] Inventors: Ronald W. George, Windermere; James G. Ohmart, Orlando; Kurt H. Irlesberger, Longwood; Lawrence L. Michaud, Casselberry; Darell E. Engelhaupt, St. Cloud, all of Fla.

[73] Assignee: Martin Marietta Corporation, Bethesda, Md.

[21] Appl. No.: 756,214

[22] Filed: Jul. 18, 1985

[51] Int. Cl.$^4$ .......................................... G01N 27/42
[52] U.S. Cl. ........................ 204/1 T; 204/3; 204/7; 204/14.1; 204/19; 204/406; 204/434
[58] Field of Search ................ 204/1 T, 3, 7, 14.1, 204/19, 434, 406

[56] References Cited

U.S. PATENT DOCUMENTS

| | | | |
|---|---|---|---|
| 2,568,713 | 9/1951 | Brenner | 73/150 |
| 2,829,517 | 4/1958 | Kushner | 73/150 |
| 3,215,609 | 11/1965 | Chapdelaine | 204/1 T |
| 3,356,597 | 12/1967 | Schmidt | 204/434 |
| 3,356,605 | 12/1967 | Schmidt | 204/434 |
| 3,437,568 | 4/1969 | Hasselmann et al. | 204/1 T |
| 3,570,449 | 3/1971 | Blecherman et al. | 118/9 |
| 4,086,153 | 4/1978 | Arigz et al. | 204/181 R |
| 4,479,980 | 10/1984 | Acorta et al. | 204/406 |

OTHER PUBLICATIONS

"The Origins of Stress in Electrodeposits I, II & III," Weil, AES Research Project 22.

Primary Examiner—Terryence Chapman
Attorney, Agent, or Firm—Gay Chin; William J. Iseman

[57] ABSTRACT

Internal stress on an object being electroplated is monitored continuously with a gauge. The gauge includes a metal receptor which is employed as a second cathode in the electrodeposition process. A separate plating current is supplied between the anode and second cathode, distinct from the separately controllable current between the anode and object being plates or electroformed. The stress on the second cathode is measured with a strain gauge, and a stress deviation from a desired plating stress is determined. The currents between the anode and first and second cathodes are adjusted in accordance with the measured internal stress on the metal receptor to achieve a desired stress condition.

The internal stress is advantageously monitored with a foil resistance strain gauge. The strain gauge is connected to a carrier disposed in parallel with the metal receptor. The carrier is rigidly connected at opposite ends to the metal receptor. A stress transmission link centrally located between ends of the metal receptor and the carrier transmits the force applied by the electroplating material on the receptor to the carrier. The strain gauge provides an indication of the stress which results from the electroplating. The currents between the anode and first and second cathodes may be controlled in accordance with this stress measurement.

13 Claims, 8 Drawing Figures

LOGIC FLOW CHART

LOGIC FLOW CHART (CONT.)

LOGIC FLOW CHART (CONT.)

LOGIC FLOW CHART (CONT.)

PROCESS MONITOR AND CONTROL CYCLES

APPARATUS AND METHOD FOR CONTROLLING PLATING INDUCED STRESS IN ELECTROFORMING AND ELECTROPLATING PROCESSES

The Government has rights in this invention pursuant to Contract No. DAAH01-82-C-1002 awarded by the Department of the Army.

The present invention relates to the process for accurately electroforming or plating metallic surfaces. Specifically, apparatus and methods are disclosed for accurately monitoring the stress produced during plating or electroforming on a surface of an object being plated or electroformed, and for controlling the plating deposition process in response to this monitored stress.

Electroforming and plating processes are known in the art for metallizing surfaces of conducting bodies. In the optical arts, it is desirable to reproduce metallic surfaces having a surface accuracy of the master mandrel which remains stable over time.

Electroforming is a precision forming fabrication technique in which a part is produced by electrodepositing the desired metal on a mandrel. This electroplated metal is then built up to the desired wall thickness and separated from the mandrel.

Prior art electroforming processes are known for making precision mechanical parts with dimensions accurate to 0.0001 inches. Electroforming optical components, however, requires a process which can produce a surface accuracy of 0.000006 inches. Obtaining these surface accuracies has been heretofore not possible due to changes in the electrolytic bath chemistry. The metal deposition which occurs during this electrochemical change induces a change in plating induced stress on the surface of the object being plated. The change in plating stress on the object produces non-uniform plated or electroformed parts.

Apparatus have been developed in the prior art to measure the internal stress conditions of the metal deposit formed during the electroplating process. One such device, known as the Brenner & Senderoff Spiral Contractometer, allows only a spot check during the continuous electroplating.

Thus, a period of time between spot checks lapses without any indication of the stress induced during the metal deposition process. The spot checks do not provide sufficient control over the electroplating to permit optical component accuracies to be obtained.

SUMMARY OF THE INVENTION

It is an object of this invention to continuously monitor the internal stress conditions of a metal deposit received by an electroplated object.

It is another object of this invention to dynamically control the current in an electroplating or electroforming process in a manner that will null the internal stress condition for metal deposited on an electroplated object.

It is a more specific object of this invention to control deposition parameters in an electroforming process to produce optical components having surface tolerances sufficient for optical imaging applications.

These and other objects are carried out by the method and apparatus in accordance with the invention. Internal stress on an object being electroformed is continuously monitored with a strain gauge. The strain gauge includes a metal receptor which is employed as a second cathode in the electroforming or electroplating process. A separate plating current is supplied between the anode and second cathode, distinct from the separately controllable current between the anode and object being plated. The stress on the second cathode is measured with a link coupling a strain gauge transducer to the metal receptor, and a stress deviation from a desired plating stress is determined. The plating currents between the anode and first and second cathodes are adjusted in accordance with the measured internal stress on the metal receptor to achieve a desired stress condition.

In an electroforming process in accordance with the preferred embodiment of the present invention, a first power supply is connected between a common anode and a mandrel over which a surface is to be electroformed, and a second power supply is connected between the anode and a metallic receptor coupled to the strain gauge transducer. A data acquisition microcontroller is connected to each power supply and the strain gauge readout circuit. A microcomputer is connected to the data acquisition microcontroller and through the data acquisition microcontroller, controls the currents supplied by each power supply in a ratio related to the relative surface areas of the metal receptor and the surface to be electroformed. The microcomputer maintains the desired current ratios of the two power supplies to generate a nulled deposit stress on the metal receptor and mandrel. The microcomputer may be programmed to terminate plating when a desired ampere hour deposition has taken place, indicating a desired metal deposition thickness has been obtained. Recording of various plating parameters such as main current, gauge current, measured internal stress and temperature is also provided in the preferred embodiment.

The internal stress is advantageously monitored with a foil resistance strain gauge. The strain gauge is connected to a carrier disposed in parallel with the metal receptor. The carrier is rigidly connected at opposite ends to the metal receptor. A stress transmission link centrally located between ends of the metal receptor and the carrier transmits the force applied by the electroplating material on the receptor to the carrier. The foil resistance strain gauge provides an indication of the stress which results from the electroplating. The currents between the anode and first and second cathodes may be controlled in accordance with this stress measurement to maintain the stress at a nominal level.

DESCRIPTION OF THE PREFERRED EMBODIMENT

Figure 1:
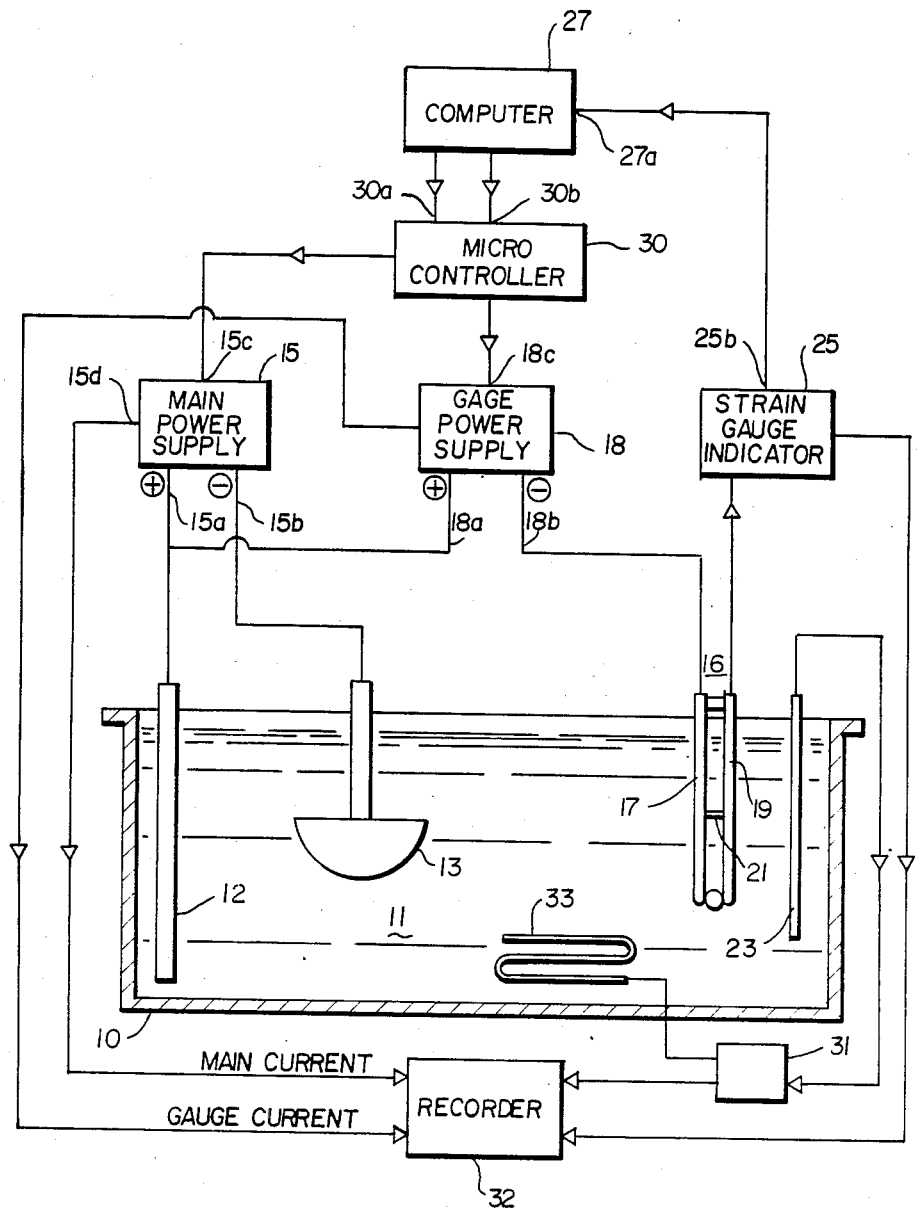
FIG. 1 is a block diagram of an apparatus for controlling an electroplating process in accordance with a preferred embodiment of the invention.

Referring now to FIG. 1, there is shown an apparatus for measuring the stress induced by plating metallic material on an object being plated. Further, FIG. 1 demonstrates a system for controlling the electroplating current by monitoring the induced stress of metal deposits received on the object. The system of FIG. 1 has been successfully used to electroform precision optical mirrors on a precision mandrel 13 surface.

The system of FIG. 1 is utilized in an electroplating process having a tank 10 which holds an electroplating solution. This solution may be, as is known to those skilled in the art, a plating solution of sulfamate nickel shown as the electroplating bath 11. The preferred solution has the following composition:

| 1 | Nickel sulfamate anhydrous | 43.6 oz/gal (327 gm/l) |
|---|---|---|
| 2 | Nickel metal | 10.2 oz/gal (76 gm/l) |
| 3 | Boric acid | 4.5 oz/gal (33.75 gm/l) |
| 4 | Corrosion agent | 0.4 oz/gal (3.0 gm/l) |
| 5 | Anti pit agent | 0.05 oz/gal (0.38 ml/l) |
| 6 | 1,3,6, Naphthalenetrisulfonic acid (NTSA) as required for zero stress | |
| 7 | Liquid corrosion additive | 2.56 oz/gal (20.0 ml/l) |

The electroforming bath of nickel sulfamate contains a known and precisely monitored additive which reduces stress in the electrodeposited nickel. Such additives as saccarin, napthaline disulfonic and trisulfonic acids are common.

Disposed in the tank 10 is an anode 12. Adjacent anode 12 is an object 13 to be electroplated or mandrel over which an electroformed surface is to be formed, which comprises a cathode. Object 13 may be any metallic object, such as a mandrel forming an optical surface which is to be electroplated within precise tolerances. A temperature probe 23 is disposed in the electroplating bath 11 to monitor temperature changes during electroplating over long periods of time. The temperature probe 23 will permit electroplating bath 11 temperatures to be monitored during the course of processing. A temperature controller is used in conjunction with the probe to maintain a precise temperature. The electroforming process also monitors precisely the additive and spontaneously formed chemical oxidation or reduction products such as azodisulfonate common to sulfamate nickel plating processes. Such a method is differential pulse polarography which provides accurate control of these and other ingredients of the electroforming solution. The mandrel 13 is cleaned and prepared for electroforming such that the electroformed deposit can be removed. The mandrel surface will have optical tolerances which permit precision mirrors to be electroformed.

In accordance with the present invention, a gauge 16 is disposed in the electroplating bath. The gauge 16 comprises a metallic receptor 17 separated from a strain gauge carrier 19. The metallic receptor 17 is connected at both ends to the strain gauge carrier 19. A force transmission link 21 connects the metallic receptor 17 and strain gauge carrier 19 at a substantially central location. The metallic receptor is cleaned as was mandrel 13 before placing in the electroplating bath 11. This configuration is an optimum design which eliminates extraneous erroneous readings.

Connected between anode 12 and cathode 13 are the positive terminals 15a and negative terminals 15b of a main power supply 15. Main power supply 15 will supply an electroplating current which will be conducted between anode 12 and cathode 13 through the electroplating bath 11. A gauge power supply 18 is similarly connected between anode 12 and metallic receptor 17 through positive and negative terminals 18a and 18b. With the separate gauge power supply 18, it is possible to supply a separate plating current to the metallic receptor 17. The respective plating currents of cathode 13 and metallic receptor 17 which functions, as can be seen by those skilled in the art, as a second cathode, are nominally selected to a value proportional to their area. The plating currents may be advantageously selected to be approximately 0.2 amperes per square inch to surface to be plated. The metallic receptor 17 will, when receiving metallic deposits during the electroplating process, impart a force through force transmission link 21 to the strain gauge carrier 19. Strain gauge carrier 19 may be conveniently read out with a strain gauge indicator 25. Thus, by monitoring the stress induced by metallic deposits on the metallic receptor 17, it is possible to determine a like stress occurring from metallic deposits on cathode 13, constituting the actual object of interest to be electroplated.

Coupling the strain gauge carrier 19 through force transmission link 21 to the metallic receptor provides an added benefit of substantially reducing the extraneous signals which occur when a single element strain measurement device is used.

Power supplies 15 and 18 are of a known type, for instance, in the case of main power supply 15, a Hewlett Packard 6295B, and in the case of the gauge power supply 18, Hewlett Packard HP6433B. These power supplies each have a control input 15c and 18c which permit the setting of the current supply between terminals 15a and 15b and 18a and 18b, such that the plating currents may be accurately controlled. Alternate brands of programmable power supplies may be used.

The strain gauge indicator 25 receives from the strain gauge carrier 19 signals produced from a foil resistance strain gauge bridge located on carrier 19. This will be more evident when referring later to FIG. 2. The differential resistance changes produced by the strain gauge bridge are converted in strain gauge indicator 25 to an analog voltage value. One strain gauge indicator which may be utilized is a type BLH 5100, manufactured by the BLH Electronics Company, known to those skilled in the instrumentation art. The strain gauge indicator 25 of the aforesaid type will provide an analog voltage output 25b indicating the tensile or compressive stress registered by the strain gauge bridge. Data acquisition microcontroller 30 includes an analog to digital converter providing an interface with microcomputer 27 through I/O port 27a.

A temperature indicating controller 31 is connected to a temperature probe 23 and provides a signal indicative of the temperature of the electroplating bath 11 and also controls the immersion heater 33. Bath temperature is preferably maintained at 43.3° C. and ±0.5° C.

A strip chart recorder 32 receives as inputs the temperature indicator 31 output signal, as well as the internal stress signal from the strain gauge indicator 25. Additionally, the main current between anode 12 and cathode 13 is recorded, as well as the gauge current between anode 12 and the metallic receptor 17. Thus, recorder 32 provides a real-time indication of the gauge deposit internal stress as the gauge current, as well as a function of temperature and the main electroplating current. From this recording it is possible to visually monitor the performance of the electroplating process during a typical manufacturing run.

Control over both gauge current and main current is effected by a microcomputer 27 which may be an HP 9826, manufactured by the Hewlett Packard Company. The operator will enter in the computer process control parameters including a starting current density (amperes/square inch), an area ratio for the cathode 13 surface and receptor 17, and a run duration expressed as ampere hours for the main power supply current. Following a 20 minute temperature normalization period for the cathode 13 and receptor 17, the computer 27 samples the strain gauge indicator output 25b for 60 seconds. The sample method may be, as is known to those skilled in the art, a systematic sample expressed mathematically as:

$$\sum_{1}^{n} \bar{x} = Xi/N$$

For the sample mean and the sample variance is:

$$\Sigma(Xi-\bar{x})^2/(n-1)$$

The sample variance then establishes a normalized stress to negate the bias effects of both agitation and temperature on the strain gauge.

Following normalization, the gauge power supply 18 is set to the specified starting current and the main power supply 15 to a current which is the product of the starting current and area ratio of the cathodes 13 and 17. The microcomputer 27 will provide parallel outputs 30a and 30b which are weighted in accordance with the area represented by the metallic receptor 17 and cathode 13. Thus, it is possible with these weighted values representing relative power supply currents, as computed by computer 27, to effect control over gauge power supply current and main power supply current. A data acquisition microcontroller 30, which may be an HP Multiprogrammer 6942A, also manufactured by the Hewlett Packard Company, will provide a necessary interface between the control inputs 18c and 15c on the gauge power supply 18, and main power supply 15. These control inputs will, in response to the sensed stress on the metallic receptor 17, increase or decrease the currents proportionally through the gauge power supply 18, and main power supply 15. Thus, the current passing between anode 12 and cathode 13, and metallic receptor 17, also functioning as a cathode in the electroplating process, may be maintained in accordance with the sensed stress resulting from metallic deposits on the metallic receptor 17.

The main power supply 15 and gauge power supply 18 are initially set at a level which will preferably yield a zero stress reading from the strain gauge indicator 25. With this as a nominal strain, it has been found in practice that consistent plating is achieved. Of course, a nominal stress of other than zero can be selected when appropriate, by making suitable adjustments to the main power supply 15c and gauge power supply 18c nominal current supply. The control system formed by the strain gauge indicator 25 output signal, computer 27 and data acquisition microcontroller 30 will thus maintain a plating current within the level to produce a metallic deposit on metallic receptor 17 within a selected nominal stress.

The process of monitoring the strain gauge output voltage and regulating the power supplies continues until the desired integral ampere hours have elapsed, corresponding to a desired deposition thickness. At that time, the computer turns the power supplies 15 and 18 off.

Figures 2A, 2B:
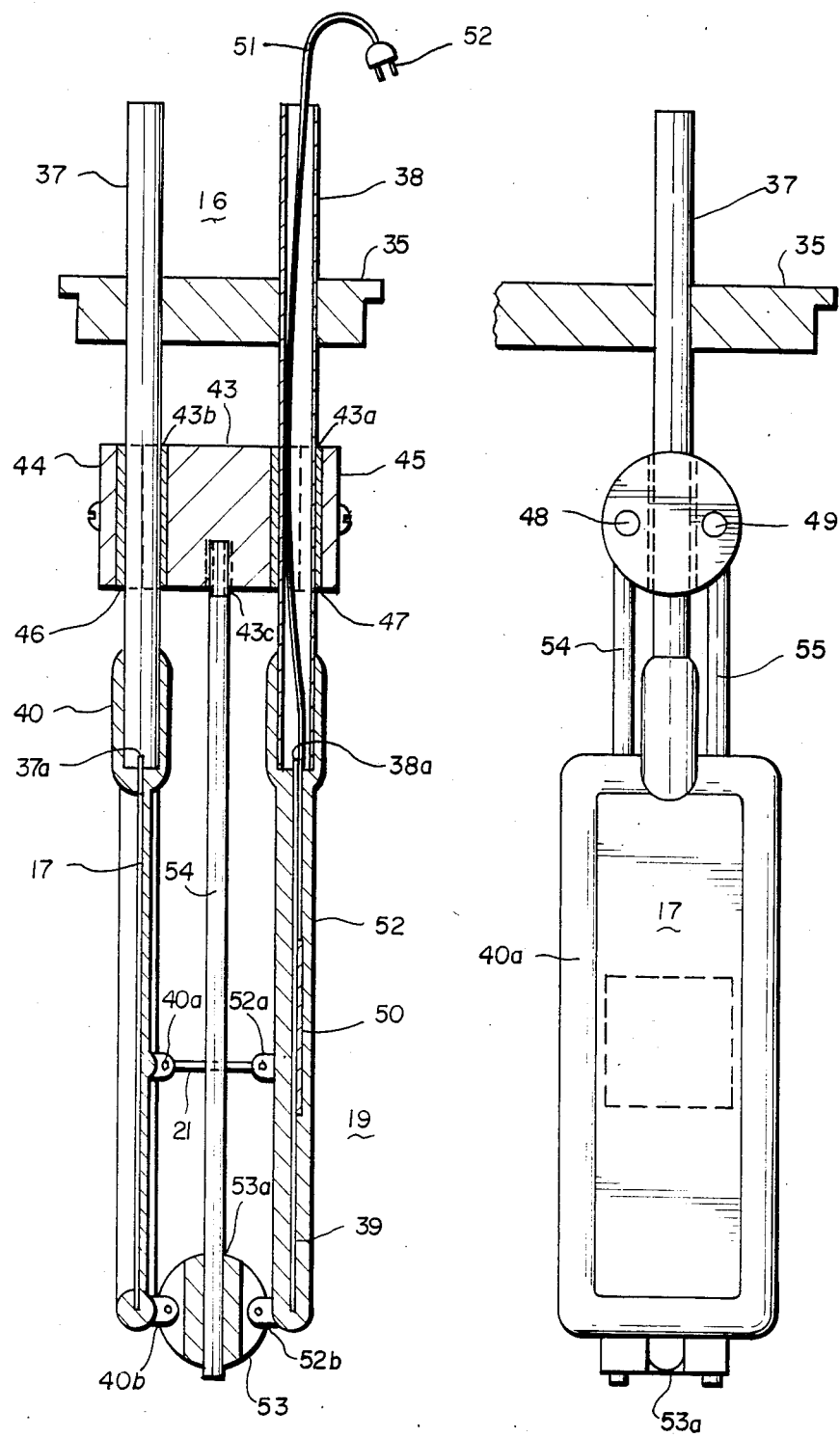
FIG. 2A is a side view of a stress measuring gauge in accordance with a preferred embodiment.
FIG. 2B is another side view of the stress measuring gauge of FIG. 2A.

Referring now to FIGS. 2A and 2B, there is shown a gauge 16 suitable for measuring the stress that occurs from a metal deposit.

Referring now to FIGS. 2A and 2B, there is shown in detail a gauge 16 in accordance with a preferred embodiment of the invention. The gauge 16 includes a pair of stainless steel conduits 37, 38 extending through a cover 35 of the tank 10 of FIG. 1. The extending stainless steel conduits 37 and 38 include at one end thereof a notch 37a and 38a. The notch 37a and 38a of each stainless steel conduit receives a metallic receptor 17 and a similar strain gauge metal carrier 39. The stainless steel conduits 37 and 38 are crimped in the area of notches 37a, 38a to fix the metallic receptor 17 and strain gauge metal carrier 39 in place. The metallic receptor 17 and strain gauge metal carrier 39 are sheets of stainless steel having approximately equal surface area.

The combination of a metallic receptor 17 and the crimped end of stainless steel conduit 37 are supported by a room temperature vulcanizing (RTV) self-curing rubber or equivalent insulating carrier 40. Insulating carrier 40 is molded to cover the side of the metallic receptor 17 facing the strain gauge carrier 19. The opposite side of the metallic receptor 17 has a molded edge 40a. An exposed area of the metallic receptor 17 is provided as shown in FIG. 2B. Thus, when metallic receptor 17 becomes a cathode by applying an appropriate potential between conduit 37 and anode 12, the exposed surface area of metallic receptor 17 receives a deposit of electroplating material. The isolation of the receptor and gauge element eliminates extraneous signals otherwise inherent.

The conduits 37 and 38 are joined together by a stainless steel clamping structure 43, and associated clamps 44 and 45. The clamping structure 43 includes a stainless steel bar having a pair of grooves 43a and 43b on opposite ends, constituting a radius equivalent to the radius of stainless steel conduits 37 and 38. Clamps 44 and 45 also have a groove with a radius substantially equal to the radius of the conduits 37 and 38. Fiberglass inserts 46 and 47 are placed over the conduits 37 and 38 to provide insulation between the grooves of clamping structure 43 and the grooves of clamps 44 and 45. Clamps 44 and 45 are secured with clamping screws 48 and 49 which are received within threads located in the clamping structure 43. The conduits 37 and 38 are thus maintained horizontally fixed with respect to each other at the top thereof by the clamps 44, 45 and clamping structure 43.

The strain gauge metal carrier 39 includes a strain gauge bridge 50, such as the resistance strain gauges manufactured by the MicroMeasurement Division Company, type MA 06062AKA. These strain gauge bridges are epoxied to the rear side of the strain gauge carrier 39, and electrical connections thereto are brought up through conductor pair 51 to a plug member 52. The strain gauge metal carrier 39 is encased in an RTV housing 52 such that no portion of the strain gauge metal carrier 39, strain gauge bridge 50 or conduit 38 is exposed to the electroplating bath.

During the molding of housing 52 and insulating carrier 40, additional connection points 40a and 40b are provided, molded in the carrier RTV housing 40. Similarly, in the molding of RTV housing 52, connection points 52a and 52b are molded as well. These connection points are connected together by a sliding Teflon link 53 and a force transmission link 21.

The remaining ends of the metallic receptor 17 and strain gauge metal carrier 39 are held rigidly by a sliding Teflon link 53. Teflon link 53 includes on two sides thereof grooves one of which, 53a is shown to accommodate two additional stiffening rods 54 and 55. Stiffening rods 54 and 55 are stainless steel and are received in openings in the clamping structure 43, one of which, 43c, is shown. The use of similar metal rigid components is required to eliminate apparent stress due to mismatched thermal expansion coefficients in structural elements. The Teflon sliding link 53 permits vertical movement between the ends of metallic receptor 17 and strain gauge metal carrier 39, while restricting horizontal movement. The Teflon link 53 is joined by connecting points 52b and 40b molded into the RTV housing 52 and metallic receptor insulating carrier 40.

During electroplating, a metal deposit will form on the metallic receptor 17 exposed to the plating solution when a voltage potential between conduit 37 and anode 12 is sufficiently high. Stress which accumulates on the metallic receptor 17 as a result of the deposition and bending of receptor 17 will be transmitted via link 21 to the RTV housing 52 and thence to the strain gauge metal carrier 39. The force so applied will be measured by the strain gauge bridge 50 as a change in resistance appearing across conductor pair 51. Plug member 52 is received in the strain gauge indicator 25 of FIG. 1. Stainless steel rods 54 and 55, in conjunction with the clamping structure 43 and sliding Teflon link 53 maintains the ends of the metal receptor 17 and carrier 39 at a fixed distance apart which will result in substantially all of the force generated by the metallic deposits being transmitted via the transmission link 21 to the strain gauge carrier 19.

Referring now to FIGS. 3A, 3B, 3C and 3D, there is shown a flow chart of the programming instructions of microcomputer 27 for implementing the process control for the previously described embodiment of the invention.

The programming comprises four (4) basic sections. The first section indicated by I, is a preparation section. This segment of the computer program instructs the system operator as to certain preprocess entries to be made for controlling the electroform process. It includes a menu to permit operator selection of the area ratios between the metallic receptor 17 and mandrel 13, as well as starting currents for the power supplies and desired process run time. The preparation section also initializes all program variables and flags.

II identifies the initializing segment of the program. This segment is entirely under repetitious control, sampling the detected stress, determining a statistical standard deviation from the sampled stress level, to be certain that the electroform system chemistry has stabilized, so that the null stress indicator will provide valid measurements of the actual stress conditions of received metal deposition. A standard nominal stress figure is derived which will serve as the system target stress.

III identifies the monitor and control segment of the program. This segment uses both conditional branching and event initiated program control. This segment of the program continually samples the stress indicator output and derives power supply currents necessary for maintaining the stress on the sample as closely as possible to the system target stress.

Finally, IV identifies the reporting segment of the computer program. The reporting segment provides printouts of pertinent statistics measured during a given electroforming process time.

Figure 3A:
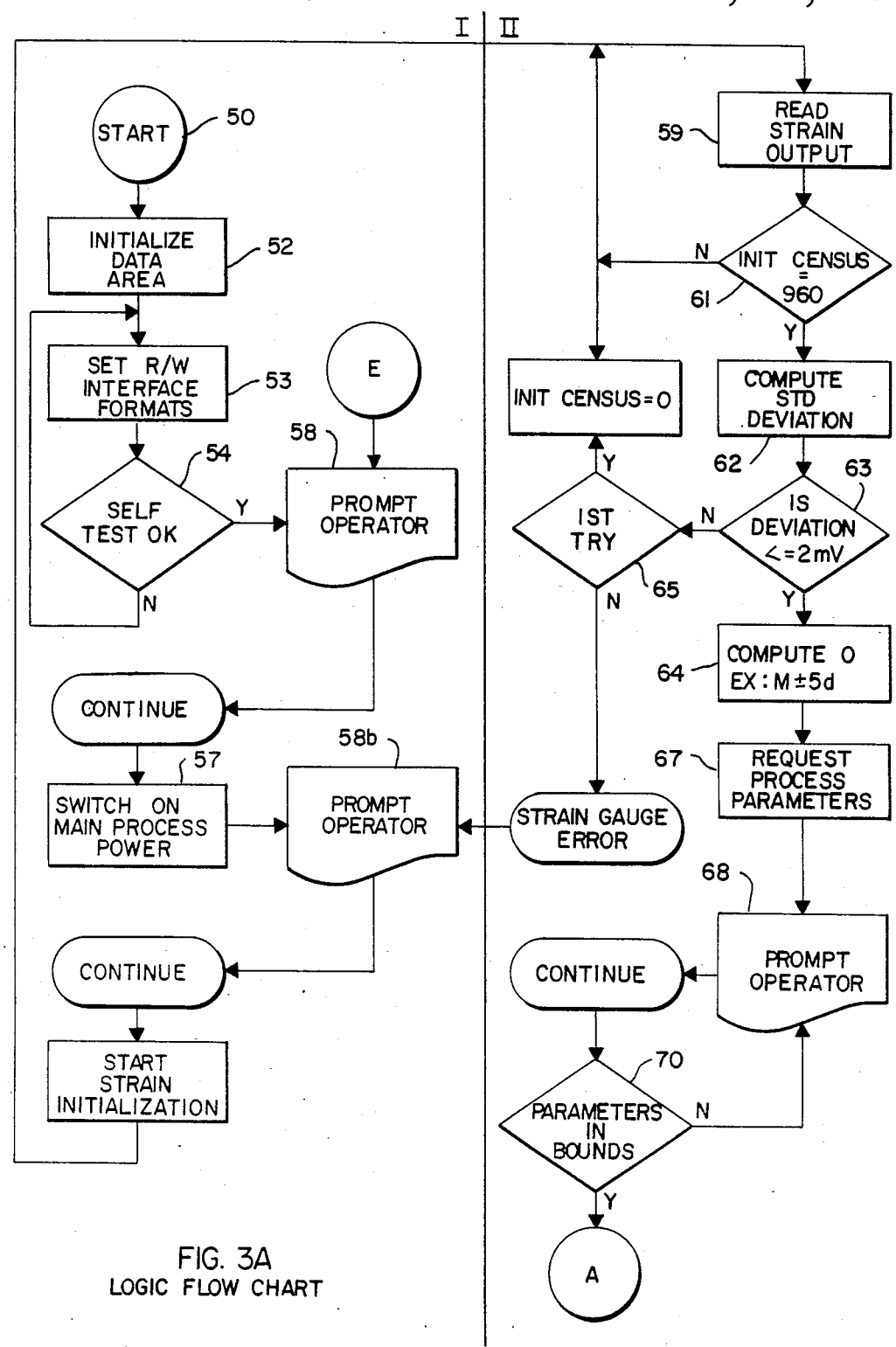
FIG. 3A illustrates the first programming segment of computer 27 for initializing process parameters.

Referring to FIG. 3A, the preparation segment of the computer program is initiated at the start indication 50. Instruction 52 will set all variables and flags in the remaining instructions to zero with the exception of the variables T, C-SETPOINT and T-SETPOINT. T controls the process run time and the number of seconds that in process statistics will be printed on a hard copy printer associated with microcomputer 27. C-SETPOINT and T-SETPOINT control the maximum high compressive current and minimum low tensile current that will be permitted by the gauge power supply 18. The maximum C-SETPOINT is 1.55 amperes and the minimum T-SETPOINT is 0.73 amps.

After the variable and flag initialization is completed, the input/output (I/O) ports of the data acquisition microcontroller are set in accordance with a subroutine 53 and a self-check performed to verify that the inputs are correctly formatted to interface with microcomputer 27. The result of decision block 54 indicates whether or not these formats have been correctly set. The self-test feature of the program merely inputs to the computer 27 through the I/O ports a known test signal and reads out through the I/O ports the results thereof to verify correct interface formatting. The operator is prompted in instruction 58 that the system has or has not been correctly formatted.

When the self-test is verified by microcomputer 27, the main power to the system is energized in step 57. The gauge and main power supplies remain off until the system strain output is determined to be constant.

The operator is again prompted to enter an area ratio for the metallic receptor 17 and mandrel 13, and the ampere hour run time.

The message on the computer 27 monitor from step 58 indicates that the system is ready to receive the mandrel to be electroplated. With the mandrel connected to the power supply, as shown in FIG. 1, the computer will make repeated sampling measurements of the output of strain gauge indicator 25 for 960 consecutive samples, constituting a statistical population. The strain gauge current is read in instruction 59. When 960 strain gauge measurements have been taken, as determined in decision block 61, a sample standard deviation is computed in instruction 62 and is expressed as $$S = \sqrt{(\sum_{1}^{n} (X_i - \bar{x})^2/(n-1)}$$

When the sample standard deviation is less than 2 millivolts, as determined in decision block 63, the program will proceed and identify this in step 64 as the target system stress point for the strain gauge reading and store this target determination in INIT.CENSUS from which subsequent measurements of strain will be compared. In the event that the standard deviation is not within the limits of decision block 63, INIT. CENSUS is set to zero and a second population group of samples will be taken, and again the standard deviation determined. If after two (2) tries of two (2) population groups of samplings have been completed, and the standard deviation is not within the limits of decision block 63, decision block 65 will indicate a strain gauge error, and display a message prompt to the operator in step 58b to indicate that the system has not settled to the point where strain gauge measurements are sufficiently reliable to permit the system to electroform precision parts.

Once the initialization of the process has been completed, instruction 67 and 68 will prompt the operator to enter process parameters such as run time, the aforementioned area ratios and a part number for the particular item being electroformed.

Once the operator enters the requested parameters, another decision block 70 determines whether these parameters are in bounds within a pre-established limit of the process.

Figure 3B:
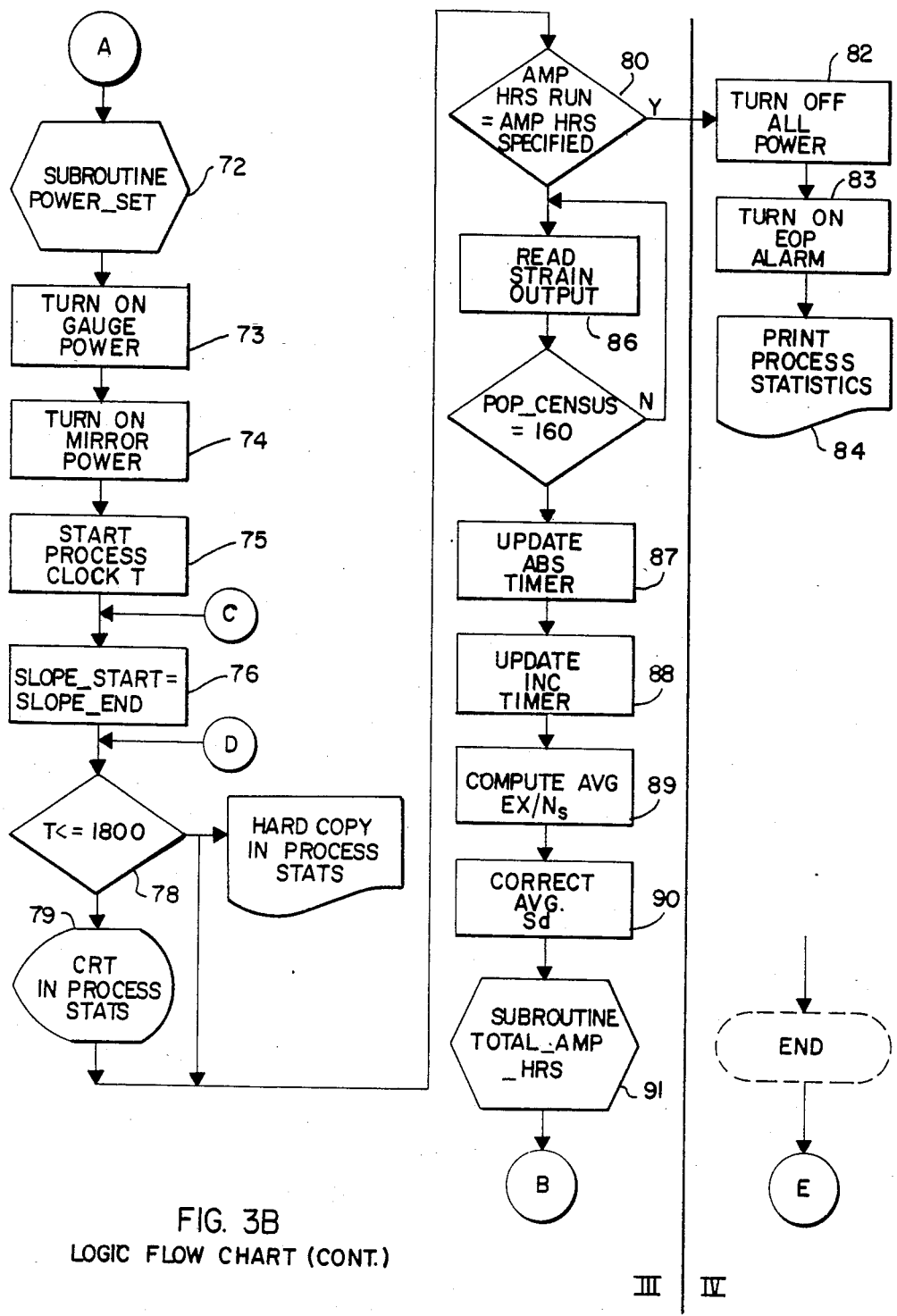
FIG. 3B illustrates the monitor and control segment of the computer program.

Referring now to FIG. 3B, there is shown a set of instructions which comprise the beginning portion of the monitor and control segment III of the program.

The first subroutine identified, 72, is the powerset portion of the program segment. The strain gauge power supply is set to a nominal current with instruction 73, and the mirror power supply with instruction 74. A process clock is started in instruction 75 which will keep track of the run time for the process.

The strain measurement is sampled 62 times in a 10 second period. The average of all of the samples taken in each of these 10 second periods will define a point representing the start or end of a line segment.

The average of the set of numerically valued strain measurements $X_1, X_2, X_3, \ldots X_n$ is expressed as $$\sum_1^n \bar{x} = Xi/n$$

As averages accumulate, startpoints and endpoints of line segments are formed. The first average becomes the startpoint of the first line segment. The second average becomes the endpoint of the first line segment. By comparing the endpoint of a line segment to the startpoint, a direction (vector) change can be determined. The endpoint then of any line segment becomes the startpoint of the next line segment. At the outset of the process converter step 76 sets the startpoint of the first line segment to the first average and does not compare to a preceding segment end because there is none.

As will become evident from the remaining description, strain gauge measurements are taken every 62.5 msec. for 10 seconds. The 10 second average of these measurements forms one data point of a line segment. The endpoint of the current segment is checked with respect to the endpoint of a previous segment to see if the stress is changing in a direction to achieve the system target stress. Entry point C of the program which returns to instruction 76 represents a condition where the slope has been found not to change between ending data points.

Decision block 78 keeps a running total of elapsed time, and outputs strain gauge reading and process statistics via hard copy for the first 1800 seconds of the proceses. After 1800 seconds have elapsed, hard copy output is terminated and instruction 78 returns control to the CRT of the computer in instruction 79 to permit continuing on-line monitoring of the process. Decision block 80 will end the electroforming process when the actual run time has equalled the specified run time. In the event the run time has elapsed, the power is turned off in instruction 82, alarms are set in instruction 83 and the process statistics are printed in instruction 84. These process statistics include, as shown in FIG. 3B, numerous process parameters which are available to the system operator.

During run time, the strain is read 62 times per second in step 86 and the sample mean is computed as:

$$\sum_1^n \bar{x} = Xi/n$$

after a population of 160 readings (sample means) have been taken, corresponding to the 10 second interval, the ABS timer and run time timer are updated. The ABS timer and run time timer are software clocks 87, 88. The ABS timer provides the 10 second intervals over which readings are taken of the strain gauge output signal.

At the conclusion of a population of 160 readings, the population mean is computed in instruction 89 as $$\sum_1^n \bar{x} = Xi/n$$

and the sample variance is corrected in step 90 by $$\Sigma(Xi-\mu)/n$$

where $\mu$ is the population mean. The elapsed time of the process is updated and dispalayed with instruction 91.

Figure 3C:
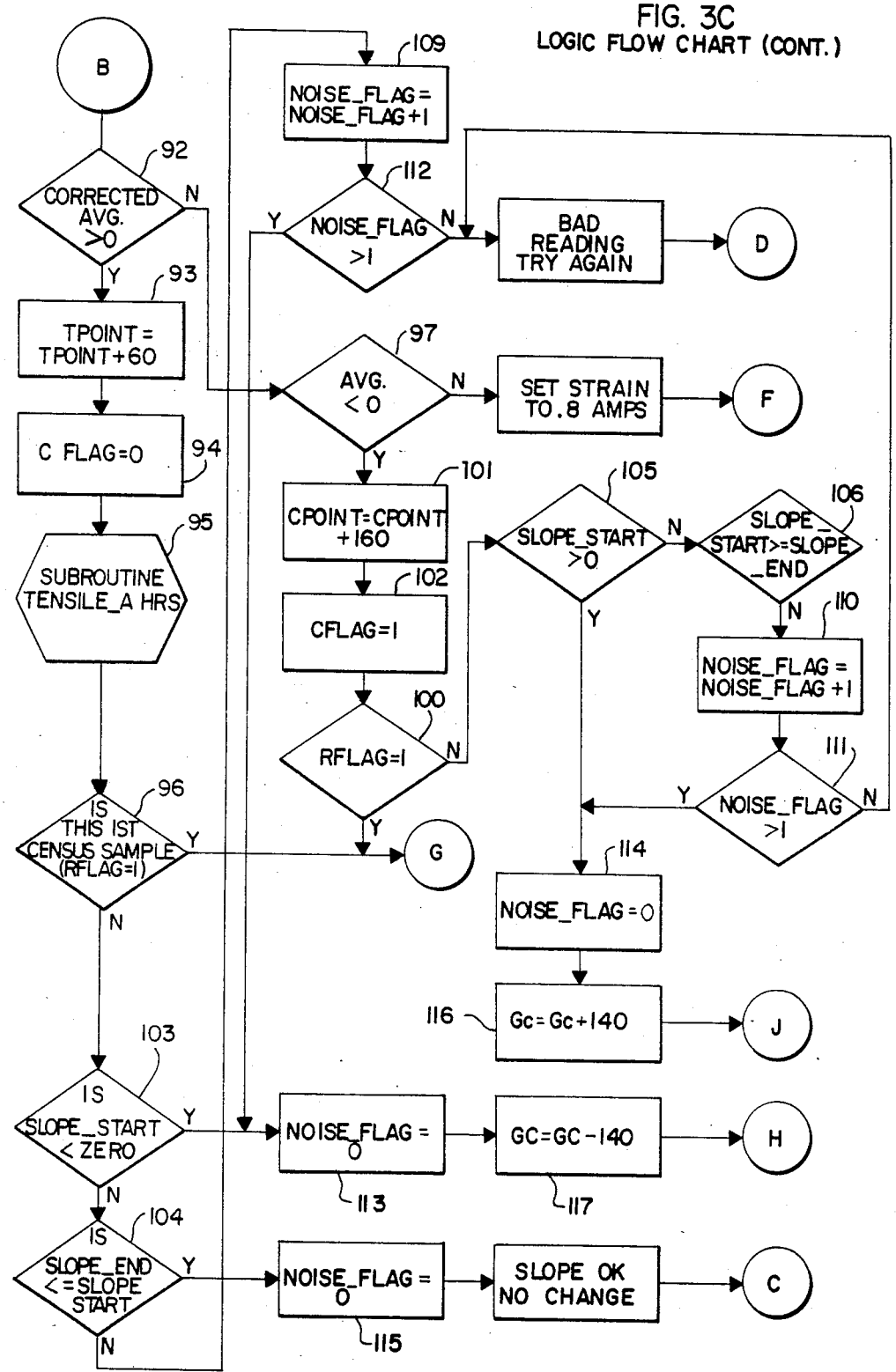
FIG. 3C illustrates the remaining instructions for the monitor and control segment of the computer program.

The monitor and control program progresses to FIG. 3C. Referring to FIG. 3C, the corrected average strain gauge reading determined in instruction 90 is compared with the target system stress strain gauge reading determined earlier in instruction 64. Comparing the corrected average strain gauge reading in decision block 92 with the target strain or stress earlier determined, indicates whether the receptor 17 is in tension or compression. When the corrected average stress reading is greater than zero, the following instructions will decrease the gauge current and the mirror power supply current in order to reduce the tension towards the target value determined in instruction 64. A counter is incremented with instruction 93 each time a corrected average strain reading indicates a tensile condition. C FLAG is set to zero in instruction 94 to indicate that the measured strain is tensile. A subroutine 95 will compute the time in which a tensile condition exists on the receptor 17, thus giving accurate process control information to the system operator when requested.

A similar count is effected in step 101 to keep track of the number of average strain measurements which are in compression. The C flag is set to 1 in the state of compression with instruction 102.

Figure 3D:
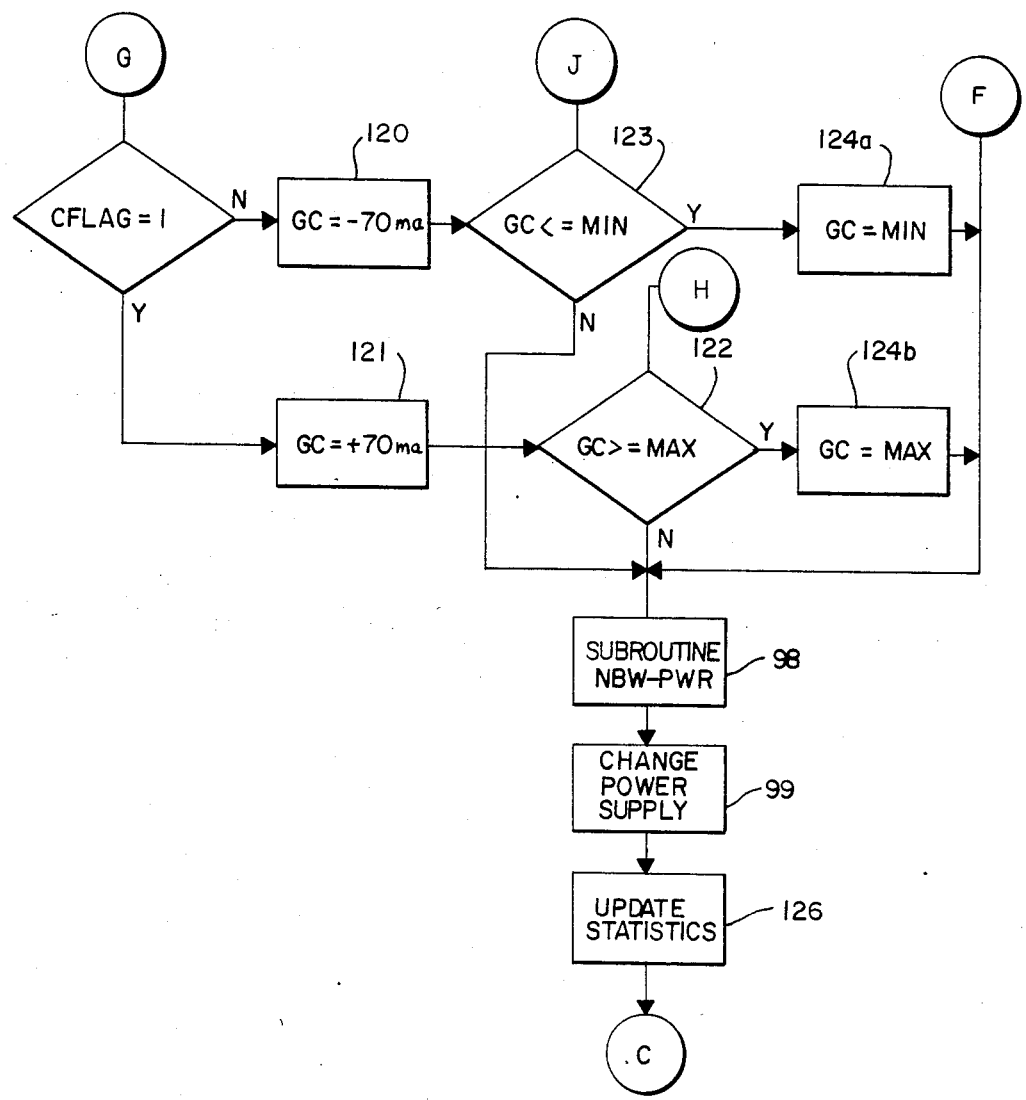
FIG. 3D illustrates the programming segment for controlling power supply currents.

In the event that the corrected average strain measurement is equal to the target stress level, decision block 97 will set the strain gauge power supply to a nominal 0.8 ampere level. Branch F, as shown in FIG. 3D, will effect the appropriate power supply current change in instructions 98 and 99 for both the mirror 15 and gauge 18 power supplies.

The remaining instructions of FIG. 3C relate to establishing a verification that the measurements made are not in error due to a "rebound condition". Rebound is a condition that is observed during strain gauge calibration that results in an unstable equilibrium of the stress indicator and occurs with a step change in power supply current. Rebounds are detected by comparing the slope of the line segments represented by data points determined by the previously described 10 second population average. If the slope of these line segments following a power supply current change is in a direction towards achieving the target system stress reading, the power supplies will remain unchanged until the slope crosses or hits the target stress. These conditions are detected in decision blocks 103, 104, 105 and 106. The two decision blocks permit the slope of the stress data points to migrate in a direction away from zero for a period of 20 seconds, two (2) 10 second population intervals, following a power supply change before re-regulation of the power supply occurs. This will avoid reacting to a spurious measurement which results from the stable equilibrium of the stress indicator.

When the strain measurements have switched from compression to tensile, the first data point indicating a tensile stress will be determined in decision block 96 and the power supplies will be decremented in instruction 120 by 70 ma. The subsequent data point will be checked in decision block 103 to determine if the following 10 seconds has moved the system back towards the zero stress condition. If the slope of the line segment formed by the consecutive data points indicates system movement away from the nominal zero stress condition, a probable rebound condition exists.

Rebound is a system instability which results from a previous step change in power supply current setting. Rebound conditions do not indicate the true system stress conditions and are to be discarded.

Decision block 104 will check the slope of the next data point, 20 seconds after the power supply change has been made following the first tensile stress indication, with the first data point. If this slope is less than the slope of the previous line segment tested in decision block 103, the slope is determined to be headed in the right direction towards zero stress level. NOISE FLAG 115 is set to zero and the current setting of power supplies 15, 18 are not changed.

In the event this line segment defined by the recent data point and the first data point has a slope greater than the previous line segment, the NOISE FLAG is set to 1 in step 109. The first time the NOISE FLAG is set to 1, corresponding to the 20 second later data point, decision block 112 determines the reading to be bad. The line segment formed by the next subsequent data point 30 seconds from the last power supply current change, and the first data point is checked in decision block 104. If the slope of the segment having this most recent data point is still greater than the previous line segment, NOISE FLAG is incremented in step 109, and checked again in decision block 112. Two consecutive line segments which indicate a stress moving away from zero stress result in a Y (yes) decision generated by decision block 112, and another step change in power supply current is effected in step 117.

The result of the foregoing is to discard two consecutivestress measurements following a step change in power supply current which indicates a further increase in the stress from a nominal zero stress. If the third stress measurement indicates a widening stress error, the power supplies are incremented.

The same type of check for a rebound condition and corresponding system control is made when the system stress switches into a compression condition.

If the average measured stress is less than zero, the next data point comprising 160 strain samples taken over a 10 second interval is taken in step 101 and the CFLAG is set to 1 in step 102. Decision blocks 100, 105, 106 make the same determination with compressing measurements as the decision blocks 96, 103, 104 did with tensile stress measurements. Flag set 110 and flag check 111 correspond to those of steps 109 and 112. Rebound conditions are effectively ignored for two 10 second intervals following a power supply change. The NOISE FLAG is set to zero in step 114 and the power supply is incremented in step 116 when two consecutive measurements of the slope of the line segments formed by second, third or fourth data points with the first data point following a power supply change indicates a widening system compression stress error. Referring to FIG. 3D, there is shown the remaining portion of the subroutine which will establish the power supply current for the gauge power supply and the mirror electroforming power supply. In the event that the first 10 second population sample of the process beginning point has been taken, as indicated by bubble G, the nominal power supplies are set at half the normal step change of 140 milliamperes to 70 milliamperes in instructions 120 and 121. The power supply settings are checked in decision blocks 122 and 123 with a maximum and minimum setting. The result of this decision, again the condition wherein the first population sample has been measured, will set the gauge power supply to its minimum or maximum condition in instruction 124a and 124b. After each population sample, when its position is checked with respect to a previous population sample, and the power supply is adjusted in light of the slope measurements to discard the rebound conditions, control returns to control bubble C, wherein additional populations in 10 second intervals are taken, and currents set based on the statistical average of these population sample until the complete run time has elapsed. Each time the control passes through C, the process statistics to be printed out are updated in instruction 126.

Figure 4:
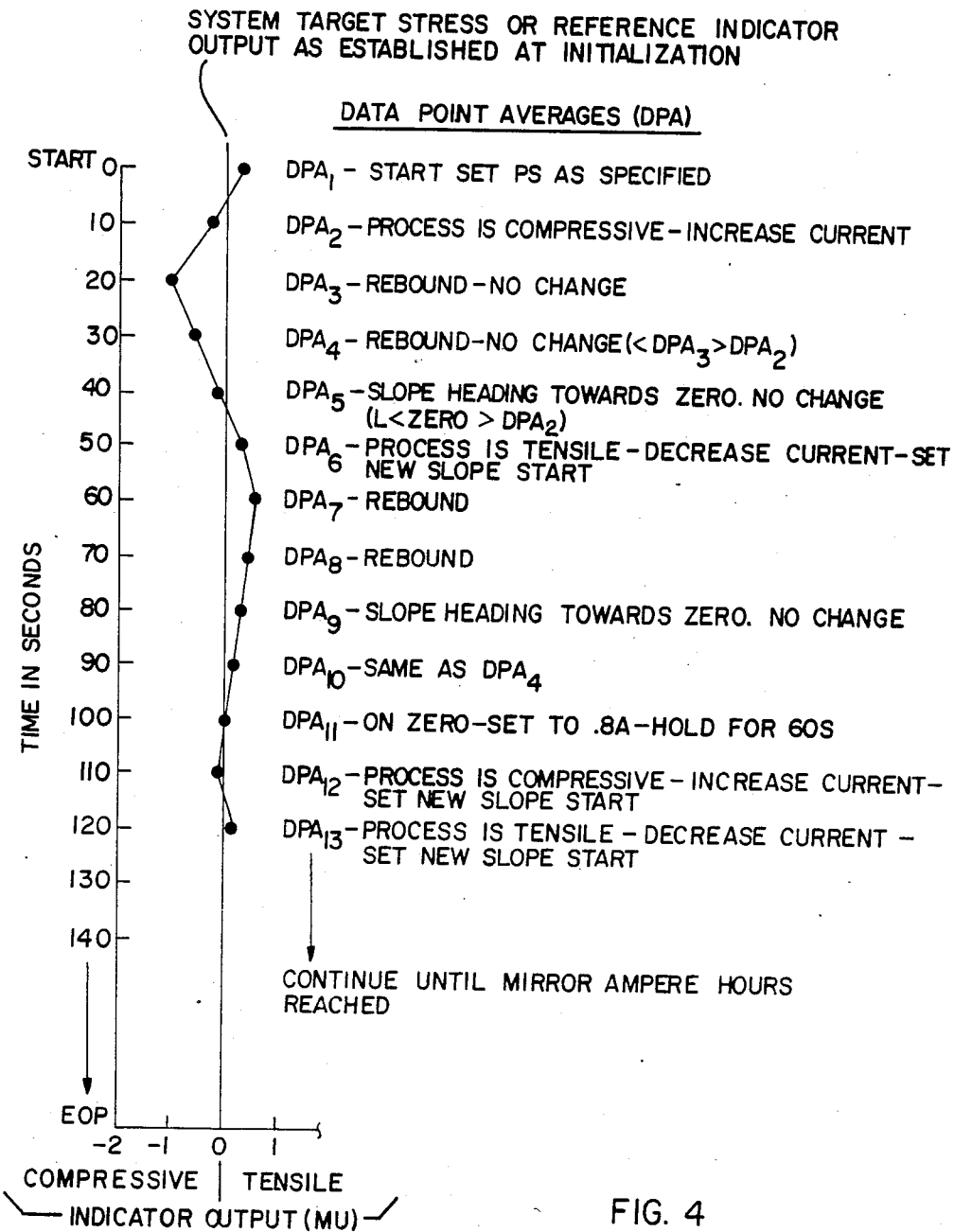
FIG. 4 illustrates the system operation over a run time to maintain the metal deposit stress to a desired minimal level.

FIG. 4 illustrates one example of how the foregoing computer instructions control the electroforming process to maintain a constant measured stress during electroforming. At the beginning system start-up point, currents are set in the power supply at the nominal levels in instructions 120, 121. When data point DPA2 is measured, representing the statistical average of the first 10 second population sample interval, a compressive stress is determined. The gauge power supply current is increased and a second data point is determined during the second 10 second population interval. The slope between the third and second data points is determined to be increasing away from the nominal stress, indicating a possible rebound condition, and the power supplies are not changed. The subsequent compressive data point DPA4 is greater than DPA2 and indicates a rebound condition preventing a change in power supply current. During the fourth 10 second population interval, DPA5 is less than DPA2 and the system is to be determined heading towards zero nominal stress, and therefore no change in power supply current is set.

As can be seen from data point 6, the stress has changed from compressive to tensile, and the current is decreased. A new slope start point is determined, and during the succeeding 10 second population interval, a rebound condition is detected since DPA7 is greater than DPA6. Following data point 7, a DPA8 in the seventh 10 second population interval is greater than DPA6 and indicates the rebound condition again.

During the eighth 10 second population interval, the stress data point DPA9 is measured to be less than DPA8 and detected as heading toward zero. No change occurs in the power supply setting since this slope is in the correct direction.

Thus, it is seen that it requires two (2) consecutive data points in 10 second periods to elapse before re-regulation of the power supply will occur. After the lapse of two (2) 10 second periods, the slope is determined for the line segments represented by the three (3) consecutive periods. Once the slope is determined as heading to zero, no current change is permitted. When the slope indicates a changing current in the wrong direction, away from the zero or reference stress for two consecutive 10 second periods, the power supplies are incremented or decremented to return the stress to the nominal desired level.

Thus, there has been described an apparatus and method for measuring the stress produced by metallic deposits formed in electroplating processes. Those skilled in the art will recognize yet other embodiments described more particularly by the claims which follow.

What is claimed is:

1. In a system for electroforming or plating, having an anode and object for plating located in an electroplating solution, an apparatus for controlling the plating induced stress on a plated object comprising:
   a DC current regulated programmable power supply connected between said anode and cathode for providing an electroplating current;
   a second planar cathode of known surface area;
   a second programmable DC power supply connected between said anode and second cathode;
   a strain gauge bridge disposed on a carrier in parallel with said second planar cathode, said carrier being rigidly supported at two ends thereof with corresponding ends of said planar cathode, said carrier coupled at a position intermediate said ends with a force transmission link to said second planar cathode, whereby plating induced stress on said second planar cathode is transmitted to said carrier;
   a strain gauge monitor connected to said strain gauge bridge for providing a signal representing said plating induced stress; and
   a computer controller connected to receive said signal, and connected to control each of said power supplies, said computer controller maintaining a plating current through each of said cathodes which produces a fixed level of plating induced stress.

2. The apparatus of claim 1 further comprising a temperature monitor for measuring the temperature of said plating bath.

3. The apparatus of claim 2 further comprising a recorder for recording during plating of said metallic receptor a signal from said strain measurement means and a signal from said temperature monitor.

4. A method for controlling the plating rate of an electroplating system having an electroform plating bath comprised of nickel sulfamate containing a monitored additive which reduces stress in electrodeposited nickel with an anode and an object to be plated as a cathode disposed therein, and a voltage source for generating a current flow between said anode and cathode, comprising:
   disposing a metallic receptor in said bath;
   establishing a current flow between said anode and metallic receptor which is related to said current flow between said anode and cathode as the ratio between the area to be placed on said object and the area of said metallic receptor;
   measuring the plating induced stresses on said metallic receptor by coupling through a force transmission link a strain gauge transducer;
   controlling the current between said anode and said cathode, and the current between said anode and said metallic receptor in response to said stress measurement from said transducer; and,
   precisely monitoring the level of said additive and any chemical oxidation or reduction products produced during electroforming.

5. The method of claim 4 further comprising:
   measuring the temperature of said plating bath; and
   recording said temperature measurements and said stress measurements.

6. The method of claim 4 wherein said currents between anode and cathode and anode and metallic receptor are supplied by separate voltage sources.

7. The method of claim 4 wherein said electroforming bath comprised of nickel sulfamate contains a known and precisely monitored additive which reduces stress in the electrodeposited nickel.

8. The method of claim 4 wherein said precisely monitoring step is carried out through differential pulse polarography.

9. A system for precision electroforming optical components comprising:
   an anode comprising a material to be electrodeposited on a metallic surface;
   a mandrel for receiving a precision deposit from said anode, said mandrel having a surface defining an optical component;
   a metallic receptor having a metal deposit receiving surface area which is a known proportion of said mandrel surface area which receives a metallic deposit from said anode;
   a strain gauge measurement means coupled to said metallic receptor generating a signal representing deposit induced stress on said metallic receptor;
   said anode, mandrel and metallic receptor disposed in a common electroforming bath of sulfamate nickel;
   a first current controlled power supply connected between said anode and mandrel;
   a second current controlled power supply connected between said anode and metallic receptor;
   a computer controller connected to receive said strain gauge measurement means generated signal, and to provide first and second current setting commands to said first and second current controlled power supplies for controlling said power supply currents in proportion to said known proportion of surface areas; said computer including programming instructions for periodically sampling said strain gauge generated signal, and generating current commands which maintain said deposit induced stress at a predetermined level.

10. The system of claim 9 wherein said computer controller further includes instructions to sample said strain gauge generated signal with a zero current level setting for said power supplies to determine a nominal strain.

11. The system of claim 10 wherein said predetermined deposit induced stress produces a measurable strain output.

12. The system of claim 9 wherein said computer controller includes instructions for sampling said strain gauge generated signals a plurality of times in a given sampling interval, and forming a statistical average of said sampled signals for each interval.

13. The system of claim 12 wherein said computer controller further includes instructions to inhibit the generation of a new current setting command until two consecutive statistical averages of said strain gauge generated signal indicate said deposit induced stress is increasing from said predetermined level.

* * * * *